United States Patent
Maeda et al.

(10) Patent No.: US 6,932,761 B2
(45) Date of Patent: Aug. 23, 2005

(54) ELECTRICALLY-BENT ENDOSCOPE

(75) Inventors: Toshinari Maeda, Hachioji (JP); Haruhiko Ueno, Hachioji (JP); Keiichi Arai, Hachioji (JP); Yuichi Ikeda, Tama (JP); Takayasu Miyagi, Hachioji (JP)

(73) Assignee: Olympus Corporation, Tokyo (JP)

( * ) Notice: Subject to any disclaimer, the term of this patent is extended or adjusted under 35 U.S.C. 154(b) by 0 days.

(21) Appl. No.: 10/673,123

(22) Filed: Sep. 26, 2003

(65) Prior Publication Data

US 2004/0073084 A1 Apr. 15, 2004

(30) Foreign Application Priority Data

Sep. 30, 2002 (JP) .................................. 2002-287853
Jul. 14, 2003 (JP) .................................. 2003-196700

(51) Int. Cl.⁷ ............................................. A61B 1/00
(52) U.S. Cl. ..................... 600/152; 600/146; 600/104; 600/117
(58) Field of Search ........................................ 600/152

(56) References Cited

U.S. PATENT DOCUMENTS

| 4,559,928 | A | * | 12/1985 | Takayama .................. 600/152 |
| 4,982,725 | A | * | 1/1991 | Hibino et al. ............... 600/117 |
| 5,159,446 | A | * | 10/1992 | Hibino et al. ................. 348/65 |
| 5,658,238 | A | * | 8/1997 | Suzuki et al. ............... 600/150 |
| 6,554,766 | B2 | * | 4/2003 | Maeda et al. ............... 600/132 |
| 2002/0087047 | A1 | * | 7/2002 | Ramijan et al. ............ 600/109 |

FOREIGN PATENT DOCUMENTS

JP  4-256724  9/1992

* cited by examiner

*Primary Examiner*—Beverly M. Flanagan
*Assistant Examiner*—Matthew J Kasztejna
(74) *Attorney, Agent, or Firm*—Scully, Scott, Murphy & Presser

(57) ABSTRACT

An electrically-bent endoscope includes a bend driving portion for bending a bending portion. The bend driving portion has a motor for generating driving force, a gear train for transmitting driving force generated in the motor, a sprocket for converting driving force of the motor to a back and forth movement of bending operation wires for bending the bending portion at the head portion of an inserting portion, and a clutch mechanism for connecting and disconnecting driving force transmitted from the gear train to the sprocket. The clutch mechanism includes a transmitting member for connecting and disconnecting the gear train and sprocket, a thrust mechanism for moving the transmitting member in the axial direction of the sprocket and a clutch operating member, connected to the thrust mechanism, for inputting instructions for connecting and disconnecting the gear train and the sprocket.

26 Claims, 13 Drawing Sheets

ELECTRICALLY-BENT ENDOSCOPE

This application claims benefit of Japanese Application Nos. 2002-287853, filed in Japan on Sep. 30, 2002 and 2003-196700 filed in Japan on Jul. 14, 2003, the contents of which are incorporated by this reference.

BACKGROUND OF THE INVENTION

1. Field of the Invention

The present invention relates to an electrically-bent endoscope for electrically bending a bending portion.

2. Description of the Related Art

Conventionally, endoscopes have been widely used. The long and narrow inserting portion of an endoscope can be inserted to the body cavity in order to observe the internal organs and to treat the internal organs as required by using treating devices laid within a treating device channel. Furthermore, the long and narrow inserting portion of an endoscope is inserted in order to observe and examine the wear and tear and/or corrosion inside of a boiler, a turbine, an engine or a chemical plant.

A bendable bending portion is connected to the base end side of the head of the long and narrow inserting portion of this kind of endoscope. A bending operation input portion such as a bending operation lever and a joystick in an operating portion is operated in order to instruct to the endoscope the bending position and bending speed of the bend as an amount of bending. In the endoscope, the bending operation wires are mechanically pulled or relaxed based on the instructed amount of bending so as to bend the bending portion.

This kind of endoscope has been proposed as an electrically-bent endoscope as disclosed in Japanese Unexamined Patent Application Publication No. 4-256724 previously filed by the present applicant, for example. The proposed electrically-bent endoscope has the bending portion electrically bent by controlling the rotation of the contained motor and by pulling or relaxing the bending operation wires by using the motor driving force.

The electrically-bent endoscope disclosed in Japanese Unexamined Patent Application Publication No. 4-256724 has a clutch mechanism for turning the driving force of the motor off. The clutch mechanism shuts off the transmission of the driving force of the motor, thus enables the bending portion to be in the angle-free mode.

SUMMARY OF THE INVENTION

According to one aspect of the invention, there is provided an electrically-bent endoscope, including a motor for generating driving force, a gear train for transmitting driving force generated by the motor, a converting member for converting the driving force of the motor to a back and forth movement of a bending operation member for bending a bending portion at the head side of an inserting portion, and a clutch mechanism having a transmitting member for connecting and disconnecting the gear train and the converting member, a thrust mechanism for moving the transmitting member in the axial direction of the converting member and a clutch operating member, connected to the thrust mechanism, for inputting instructions for connecting and disconnecting between the gear train and the converting member, the clutch mechanism connecting and disconnecting the driving force transmitted from the gear train to the converting member.

According to another aspect of the invention, there is provided an electrically-bent endoscope, including a motor for generating driving force for bending a bending portion at the head portion of an inserting portion, a gear train for transmitting driving force generated in the motor, a sprocket for converting driving force of the motor to a back and forth movement of a bending operation wires, and a clutch mechanism having a transmitting member for connecting and disconnecting the final level of the gear train and the sprocket, which are provided coaxially, a thrust mechanism for moving the transmitting member back and forth in the axial direction of the sprocket and a clutch operation knob, connected to the thrust mechanism, for inputting instructions for connecting and disconnecting the final level of the gear train and the sprocket.

According to another aspect of the invention, there is provided an electrically-bent endoscope, including a motor for generating driving force, a driving force transmitting portion for transmitting driving force generated in the motor, a converting portion for converting driving force of the motor to a back and force movement of a bending operation member for bending a bending portion at the head of an inserting portion, a clutch portion including a transmitting member for connecting and disconnecting the driving force transmitting portion and the converting portion, a thrust portion for moving the transmitting member in the axis direction of the converting portion, and an operating portion, connected to the thrust portion, for inputting instructions for connecting and disconnecting the driving force transmitting portion and the converting portion, the clutch portion connecting and disconnecting driving force transmitted from the driving force transmitting portion to the converting portion.

According to another aspect of the invention, there is provided an electrically-bent endoscope, including a motor, driving force transmitting means for transmitting driving force generated in the motor, converting means for converting driving force of the motor to a back and force movement of a bending operation member for bending a bending portion at the head of an inserting portion, clutch means including a transmitting member for connecting and disconnecting the driving force transmitting means and the converting means, means for moving the transmitting member in the axis direction of the converting means, and operating means, connected to the means, for inputting instructions for connecting and disconnecting the driving force transmitting means and the converting means, the clutch means connecting and disconnecting driving force transmitted from the driving force transmitting means to the converting means.

Other features and advantages of the present invention will become apparent from the following description.

DETAILED DESCRIPTION OF THE PREFERRED EMBODIMENTS

A first embodiment of the invention will be described below with reference to drawings.

FIGS. 1 to 15 relate to the first embodiment.

Figure 1:
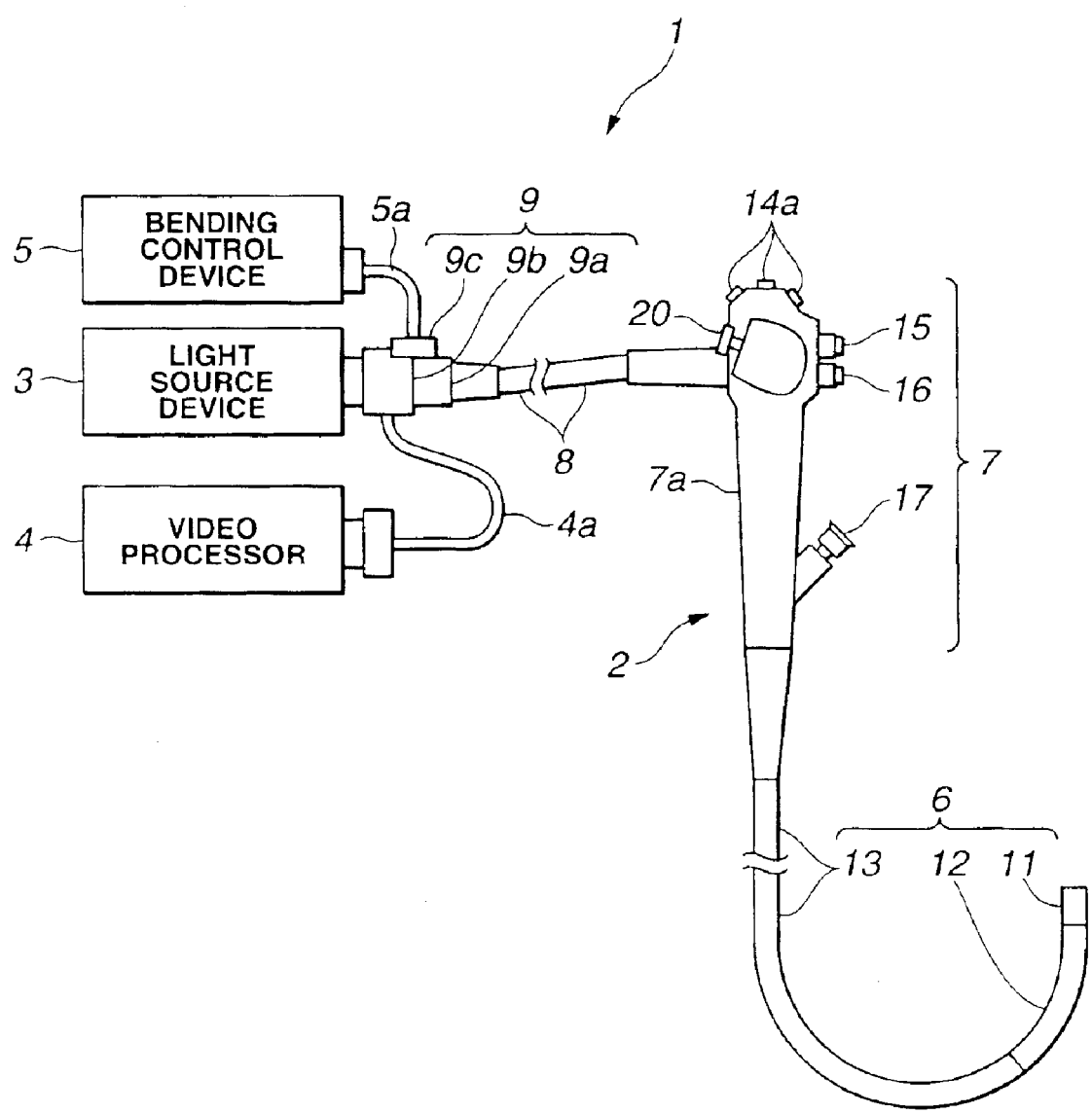
FIG. 1 is an entire construction diagram showing an electrically-bent endoscope apparatus including a first embodiment of the invention.

An electrically-bent endoscope apparatus 1 having the first embodiment of the invention as shown in FIG. 1 includes an electrically-bent endoscope 2, a light source device 3, a video processor 4, and a bending control device 5. The electrically-bent endoscope 2 includes a bend driving portion (see FIG. 2) for electrically bending a bending portion, which will be described later, of the head side of the inserting portion. The light source device 3 supplies illumination light to the electrically-bent endoscope 2. The video processor 4 performs signal processing on an imaging portion, which will be described later, within the electrically-bent endoscope 2. The bending control device 5 controls the driving of the bend driving portion of the electrically-bent endoscope 2. The video processor 4 is connected to a monitor, not shown, outputs video signals to the monitor and causes the monitor to display endoscope images.

The electrically-bent endoscope 2 is connected to the base end side of the inserting portion 6 and further includes an operating portion 7 also functioning as a grasping portion 7a. The electrically-bent endoscope 2 further includes a soft universal cord 8 extending from the side of the operating portion 7. The universal cord 8 contains a light guide and/or a signal cable, not shown. The universal cord 8 has a connector portion 9 at the end. The connector portion 9 includes a light guide connector (called LG connector hereinafter) 9a at the end and a video connector 9b and angle connector 9c on the side of the LG connector 9a. The LG connector 9a is removably connected to the light source device 3. The video connector 9b is removably connected to a connecting cable 4a of the video processor 4. The angle connector 9c is removably connected to a connecting cable 5a of the bending control device 5.

The endoscope inserting portion 6 (which is the inserting portion 6 of the electrically-bent endoscope 2) includes a head portion 11, a bendable bending portion 12 and a flexible tube portion 13. The head portion 11 is provided at the head of the endoscope inserting portion 6. The bending portion 12 is provided at the base end side of the head portion 11. The flexible tube portion 13 is provided at the base end side of the bending portion 12 and is long and flexible.

The endoscope operating portion 7 (which is the operating portion 7 of the electrically-bent endoscope 2) has the grasping portion 7a at the base end side. The grasping portion 7a is a part to be grasped by a user. The endoscope operating portion 7 has multiple video switches 14a for remotely operating the video processor 4 above the grasping portion 7a. The endoscope operating portion 7 further includes an air/water feeding button 15 and a suction button 16 on the side. The air/water feeding button 15 controls air-feeding and water feeding operations. The suction button 16 controls suction operations.

The endoscope operating portion 7 further includes a treating device inserting port 17 near the front end of the grasping portion 7a. Treating devices such as a biopsy forceps are inserted from the treating device inserting port 17. The treating device inserting port 17 communicates with a treating device inserting channel, not shown, inside. A treating device, not shown, such as a forceps, is inserted from the treating device inserting portion 17, and the head side of the treating device from a channel opening at the head portion 11 through the internal treating device inserting channel in order to perform a biopsy.

The endoscope operating portion 7 further includes a bending operation inputting portion 20 such as a joystick, a trackball or the like to be manipulated for bending the bending portion 12.

Figure 2:
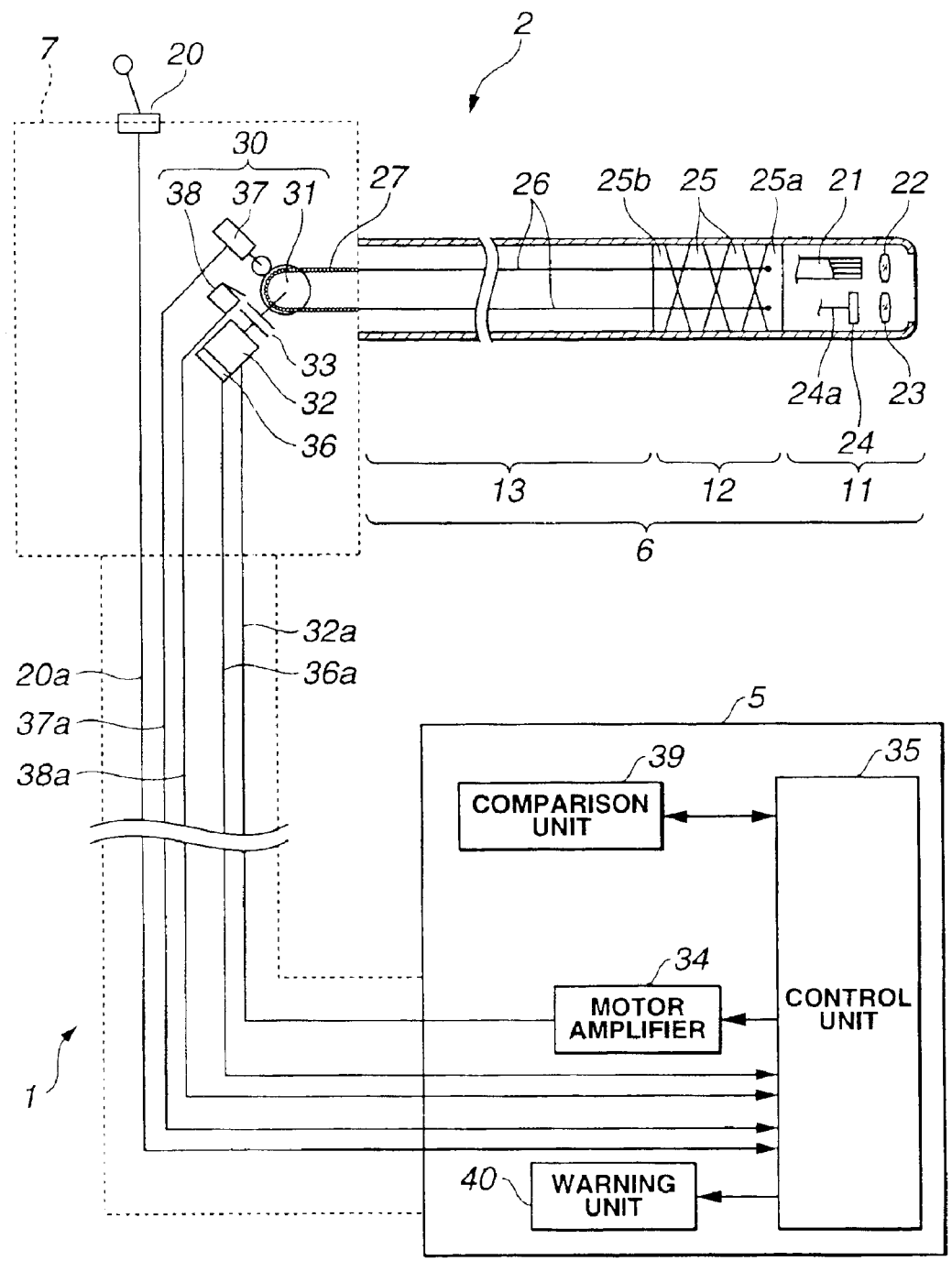
FIG. 2 is a schematic construction diagram showing the electrically-bent endoscope apparatus in FIG. 1.

As shown in FIG. 2, the electrically-bent endoscope 2 has a light guide 21 for transmitting illumination light within the inserting portion 6. The base end of the light guide 21 extends to the connector portion 9 of the universal cord 8 through the operating portion 7 so that illumination light from a light source lamp, not shown, in the light source device 3 can be transmitted. The illumination light transmitted from the light guide 21 illuminates an object such as an affected part from the head surface of an illumination window, not shown, fixed at the inserting portion head portion 11 through an illumination optical system 22.

The object image of the illuminated object is captured from an observation window, not shown, adjacent to the illumination window. The captured object image is imaged and optoelectronically converted to imaging signals by an imaging device 24 such as Charge-coupled device (CCD) through an objective optical system 23.

Then, the imaging signals are transmitted through a signal cable 24a extending from the imaging device 24 and reach the video connector 9b of the universal cord 8 through the operating portion 7. Then, the imaging signals are output to the video processor 4 through the connecting cable 4a.

The video processor 4 performs signal processing on the imaging signals from the imaging device 24 of the electrically-bent endoscope 2, generates standard video signals and causes the monitor to display the endoscope images.

The base end portion of the inserting portion head portion 11 of the electrically-bent endoscope 2 is connected to a bend bridge 25a at the extreme end of multiple bend bridges 25. The multiple bend bridges 25 are included in the bending portion 12 and can rotate independently from each other. On the other hand, the last bridge 25b of the bend bridges 25 is connected to the head side of the flexible tube portion 13.

The inserting portion 2 has bending operation wires 26 inside. The bending operation wires 26 are bending operation members for bending the bending portion 12 vertically and horizontally in the observation view. The heads of the bending operation wires 26 are fixed and are held at the bend bridge 25a at the extreme end by brazing, for example, at the vertical and horizontal positions of the bending portion 12. Thus, by pulling and relaxing the bending operation wires 26 corresponding to the directions, the bending portion 12 bends in a desired direction and the head portion 11 is directed in a desired direction.

The base ends of these bending operation wires 26 are connected to chains 27. These chains 27 are pulled and are relaxed by the bend driving portion 30 so as to electrically bend the bending portion 12. The bending operation wires 26 and the chains 27 are shown vertically or horizontally in FIG. 2.

The bend driving portion 30 has a motor 32 and a sprocket 31. The motor 32 generates driving force for bending the bending portion 12. The sprocket 31 converts the driving force of the motor 32 to back and forth movement of the bending operation wires 26 and pulls and relaxes the chains 27.

The bend driving portion 30 has a clutch mechanism 33, between the sprocket 31 and the motor 32, for connecting and disconnecting the driving force of the motor 32. Thus, the bend driving portion 30 shuts off the transmission of the driving force of the motor 32 by using the operation of the clutch mechanism 33 and can therefore have any angles. The clutch mechanism 33 is manually operated through a clutch operation knob, which will be described later. The clutch mechanism 33 may be controlled by a control unit, which will be described later, in the bending control device 5.

The bend driving portion 30 has two vertical and horizontal motors 32 (and an encoder 36, which will be described later), the sprocket 31 and the clutch mechanism 33 (and a potentiometer 37, which will be described later) and these two pairs are provided in the gearbox, which will be described later. In FIG. 2, the bend driving portion 30 has one of the vertical and horizontal motors 32 (and the encoder 36), the sprocket 31 and the clutch mechanism 33 (and the potentiometer 37).

A signal line 32a extending from the motor 32 reaches the angle connector 9c of the universal cord 8 and supplies motor driving signals from a motor amplifier 34 in the bending control device 5 through the connecting cable 5a. The motor amplifier 34 is connected to the control unit 35 and is controlled and is driven by the control unit 35.

The encoder 36 is mounted to the motor 32. The encoder 36 functions as a second detector for detecting the rotating position about the motor axis. The signal line 36a extending from the encoder 36 reaches the angle connector 9c of the universal cord 8 and outputs rotating position signals indicating the detected rotating position of the motor 32 to the control unit 35.

The sprocket 31 is a converting member for converting the rotational movement of the motor 32 to back and forth movement of the bending operation wires 26. The potentiometer 37 is mounted to the sprocket 31. The potentiometer 37 functions as a first detector for detecting the rotating position. The signal line 37a extending from the potentiometer 37 reaches the angle connector 9c of the universal cord 8 and outputs rotating position signals indicating the detected rotating position of the sprocket 31 to the control unit 35.

A clutch operation detecting switch 38 detects whether the clutch mechanism 33 is turned on and off or not. Also, the signal line 38a extending from the clutch operation detecting switch 38 reaches the angle connector 9c of the universal cord 8 and outputs clutch operation signals indicating the detected operations of the clutch mechanism 33 to the control unit 35.

As described above, the electrically-bent endoscope 2 has the bending operation input portion 20 such as a joystick, a trackball or the like at the grasping portion 7a of the operating portion 7. The signal line 20a extending from the bending operation input portion 20 reaches the angle connector 9c of the universal cord 8 and outputs bending operation signals indicating the input bending operation to the control unit 35.

The control unit 35 controls the motor amplifier 34 to drive the motor 32 in accordance with the bending operation signals from the bending operation input portion 20 and based on signals from the encoder 36 and the potentiometer 37. Thus, the bending portion 12 is bent.

The bending control device 5 further includes a comparison unit 39 and a warning unit 40. The comparison unit 39 always compares information from the encoder 36. The warning unit 40 warns an operator-based on the information from the comparison unit 39.

Thus, the bending control device 5 obtains information of the encoder 36 mounted at the motor axis and the information of the potentiometer 37 mounted at the sprocket 31 and always compares these kinds of information in the comparison unit 39. When the bending portion 12 reaches the bending limit, the bending control device 5 detects it. Then, the warning unit 40 warns the operator. Furthermore, in the bending control device 5, the control unit 35 outputs a stop signal to the motor amplifier 34 to stop the motor 32.

The rotational angle of the sprocket 31 and the rotational angle of the potentiometer 37 have one-to-one correspondence independently from the transmission state of the clutch mechanism 33.

Next, a detail construction of the bend driving portion 30 will be described.

Figure 3:
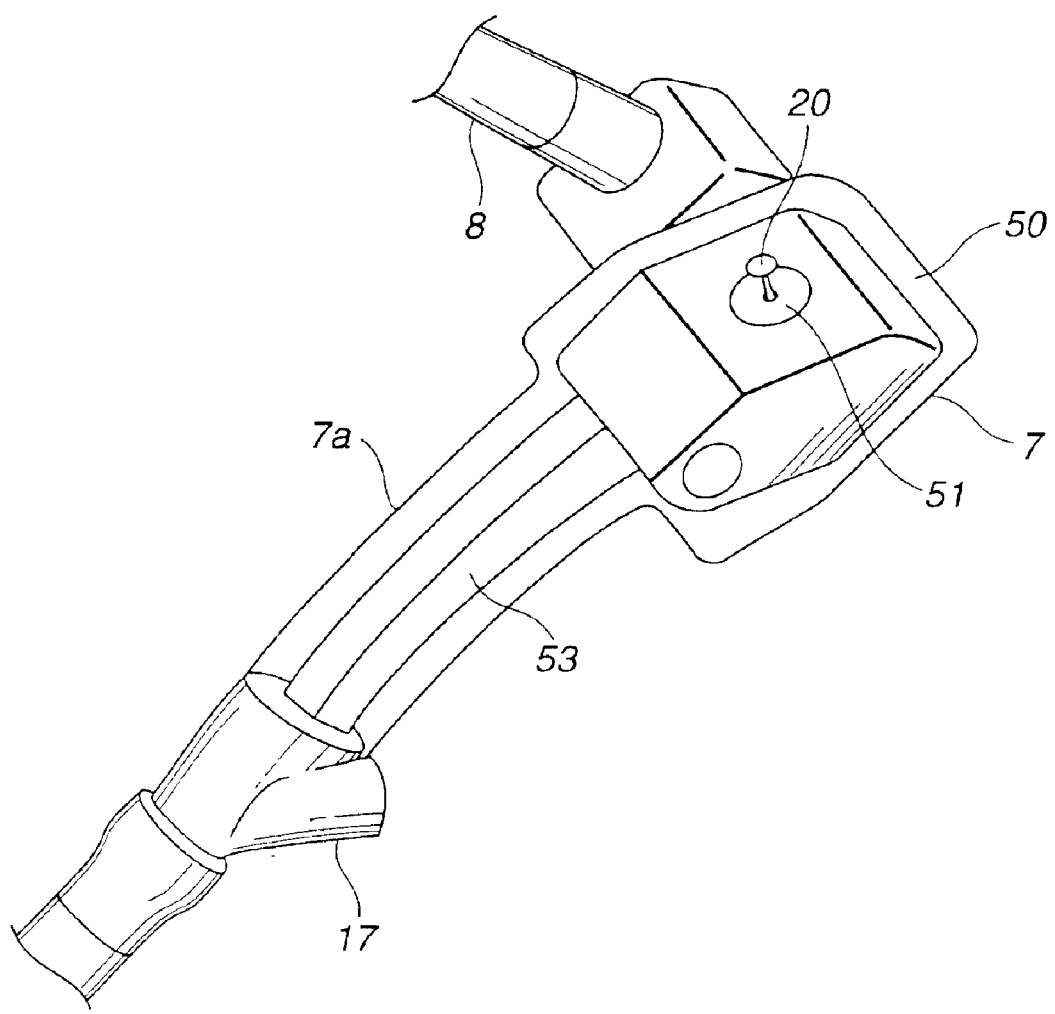
FIG. 3 is a schematic diagram showing a gearbox in the electrically-bent endoscope in FIG. 2.

As shown in FIG. 3, the bend driving portion 30 is stored in the gearbox 50 within the operating portion 7 of the electrically-bent endoscope 2.

The gearbox 50 has a bending operation portion 51 having the bending operation input portion 20 such as a joystick, a trackball or the like. The gearbox 50 further stores the chains 27 and the bending operation wires 26 in a wire pulling mechanism portion 53 extending from the rear end.

Figure 4:
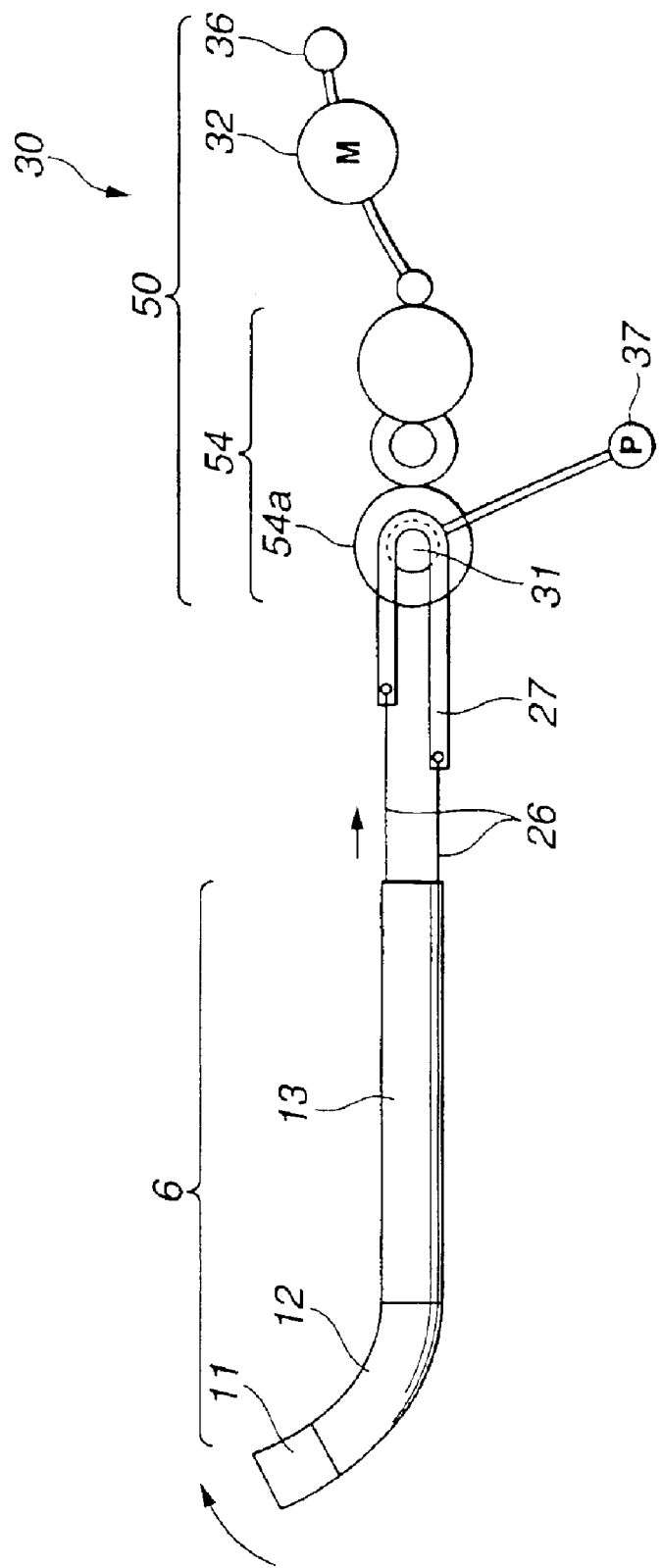
FIG. 4 is a schematic diagram showing a construction of a bend driving portion stored in the gearbox in FIG. 3.

As shown in FIG. 4, the gearbox 50 further stores the motor 32, sprocket 31, encoder 36, and potentiometer 37 in the bend driving portion 30. The bend driving portion 30 has a gear train 54 in the gearbox 50. The gear train 54 transmits driving force generated by the motor 32 to the sprocket 31.

According to this embodiment, the final level gear 54a of the gear train 54 and the sprocket 31 are located coaxially in the bend driving portion 30 as described later. The clutch mechanism 33 for connecting and disconnecting the driving force to be transmitted from the gear train 54 to the sprocket 31 is provided at the final level of the gear train 54. FIG. 4 shows the vertical or horizontal bend driving portions 30.

Figure 5:
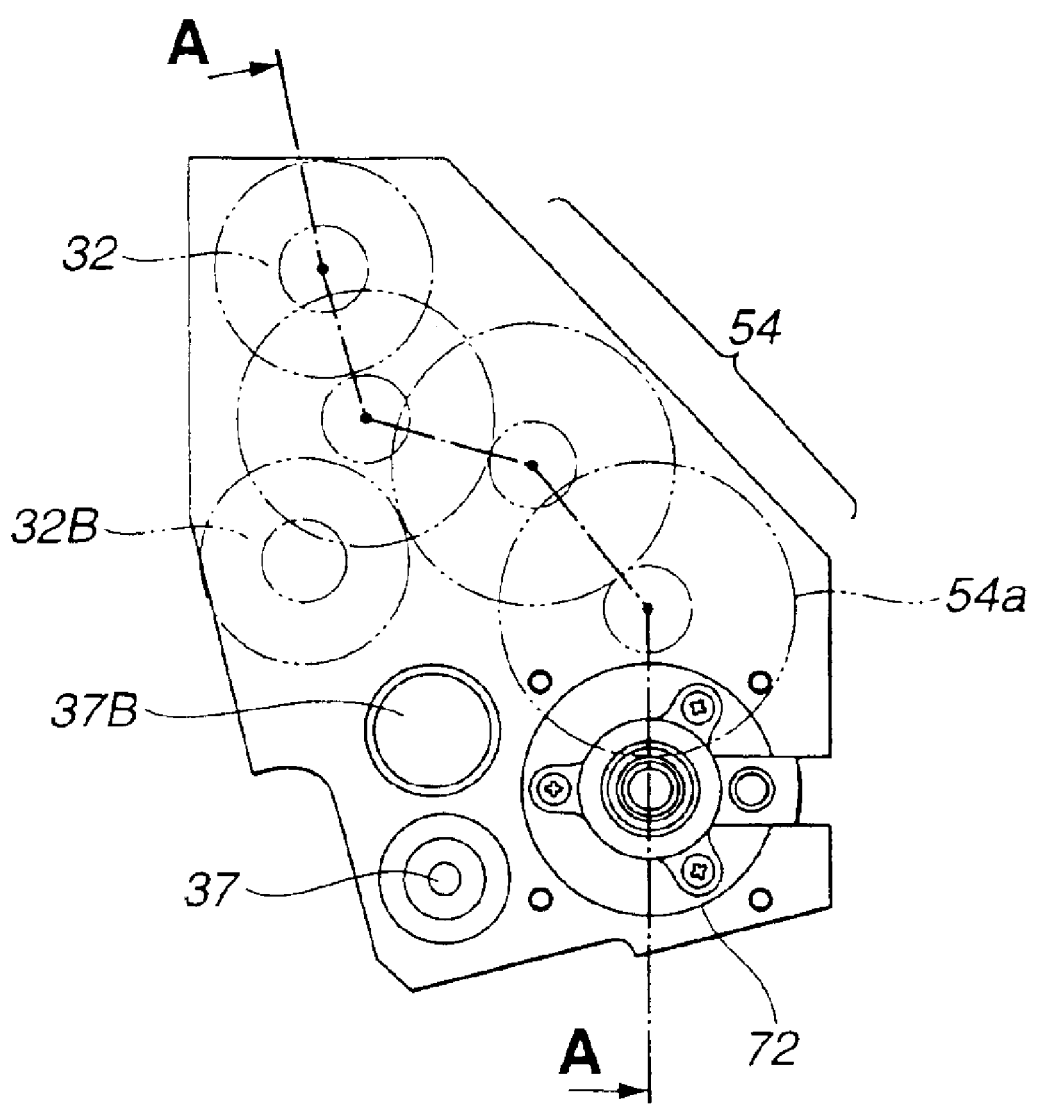
FIG. 5 is an explanatory side elevation diagram of the gearbox in FIG. 3.
Figure 6:
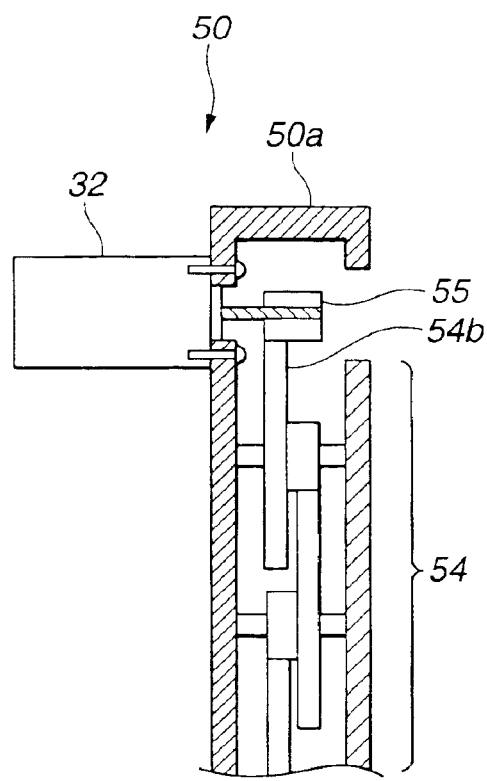
FIG. 6 is a section diagram taken at line A—A in FIG. 5.

As shown in FIGS. 5 and 6, the gear train 54 includes multiple gears including a first gear 54b and a final level gear 54a. The first gear 54b engages with a pinion 55 of the motor 32 in the gear train 54. The final level gear 54a engages with the gear 54b to engage with the sprocket 31. The gear train 54 has a function for reducing the speed and amplifying the driving force from the motor 32. Then, the gearbox 50 covers the entire gear train 54 and can prevent the catching of the other organs within the endoscope and the scattering of the grease coated over the gears. The reference numeral 32B indicates a second motor while the reference numeral 37B indicates the second potentiometer. The letter "B" is given to each of second members hereinafter, and one of these members will be mainly described for the convenience of the explanation.

Figure 7:
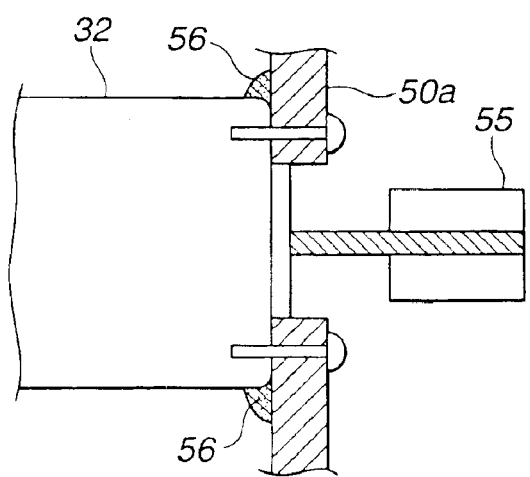
FIG. 7 is an enlarged diagram of a motor mounting part in FIG. 6.

The motor 32 is screwed to a frame 50a of the gearbox 50 as shown in FIG. 7 and can be easily removed from the gearbox 50 together with the encoder 36. Thus, the gearbox 50 can be removed together with the encoder 36 from an opening, not shown, by approaching the gearbox 50 from the opening and unscrewing the screw fixing the motor 32.

The motor 32 facing toward the frame 50a of the gearbox 50 is coated with a heat transmitting agent 56 such as a heat compound. Thus, the motor 32 can diffuse the generated heat to the frame 50a of the gearbox 50 through the heat transmitting agent 56, and the gearbox 50 can be a heat sink. Therefore, the gearbox 50 does not have to have another heat sink and can be reduced in size.

The motor 32 is constructed by press-fitting the pinion 55 into the motor axis. Thus, the EOG (ethylene oxide gas)-resistance of the motor 32 can be improved since the motor axis is not exposed to EOG during the sterilization.

Figure 8:
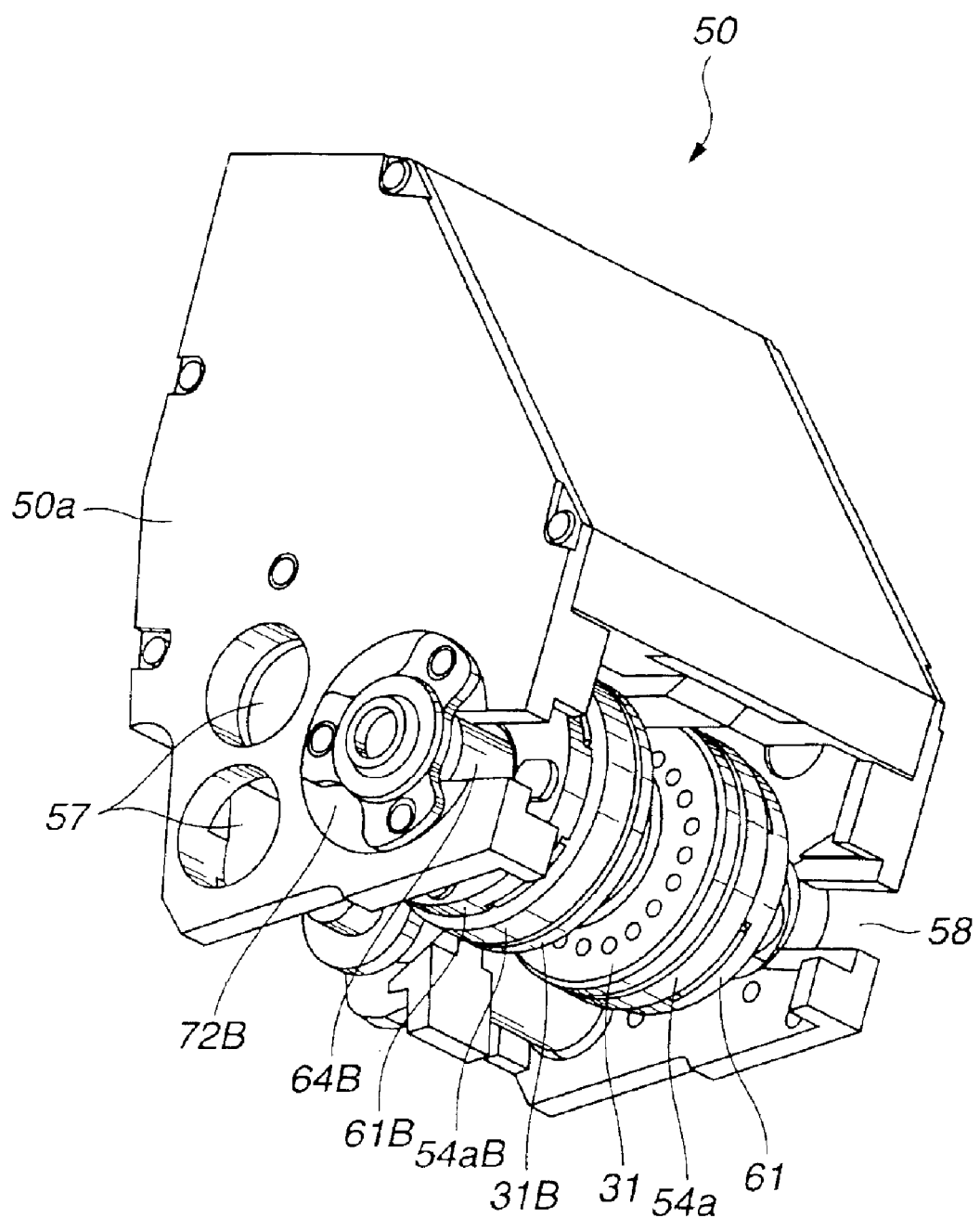
FIG. 8 is a perspective diagram showing a clutch mechanism mounted to the gearbox.

As shown in FIG. 8, the gearbox 50 has an opening portion 57 from which the potentiometer 37 can be removed. Thus, a jig can be brought to the nut fixing the potentiometer 37. Therefore, the potentiometer 37 can be fixed securely, and the repairability of the gearbox 50 can be improved in relation to the influence on the life due to the abrasion. The gear of the potentiometer 37 contains aluminum instead of resin. Therefore, irrespective of metal, the potentiometer 37 is lightweight, rigid and good in adherability and can be fixed to the potentio-axis more securely.

The gearbox 50 has a long slot opening 58, for example, from which the clutch mechanism 33 can be removed. The clutch mechanism 33 is screwed to the frame 50a of the gearbox 50 and can be easily removed from the gearbox 50. Thus, the gearbox 50 can be slid and be removed from the opening portion 58 by approaching it from the opening portion 58 and unscrewing the screw fixing the clutch mechanism 33.

In this way, in the gearbox 50, not only the repairability of the motor 32 having the higher number of revolutions (causing the abrasion of the brush portion) and the heavy-loaded clutch mechanism 33 can be improved. Furthermore, since the opening portion 38 has a combination of a long slot and a hole larger than the width of the long slot instead of a simple long slot, the repairability can be improved. Still further, the distance between gears can be obtained accurately.

Next, a detail construction of the clutch mechanism 33 will be described with reference to FIGS. 9 to 14.

Figure 9:
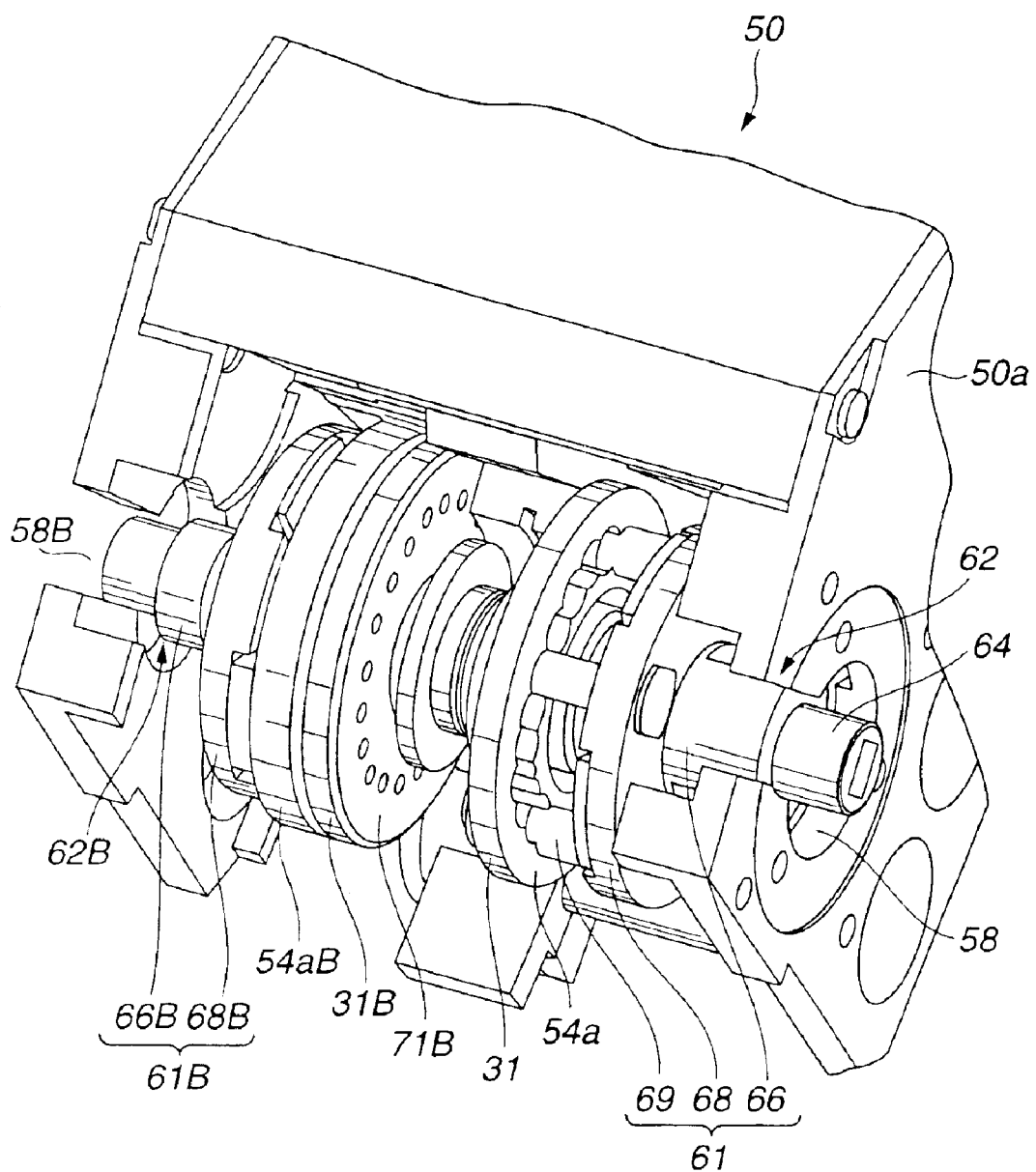
FIG. 9 is an enlarged diagram of the main part of FIG. 8.
Figure 10:
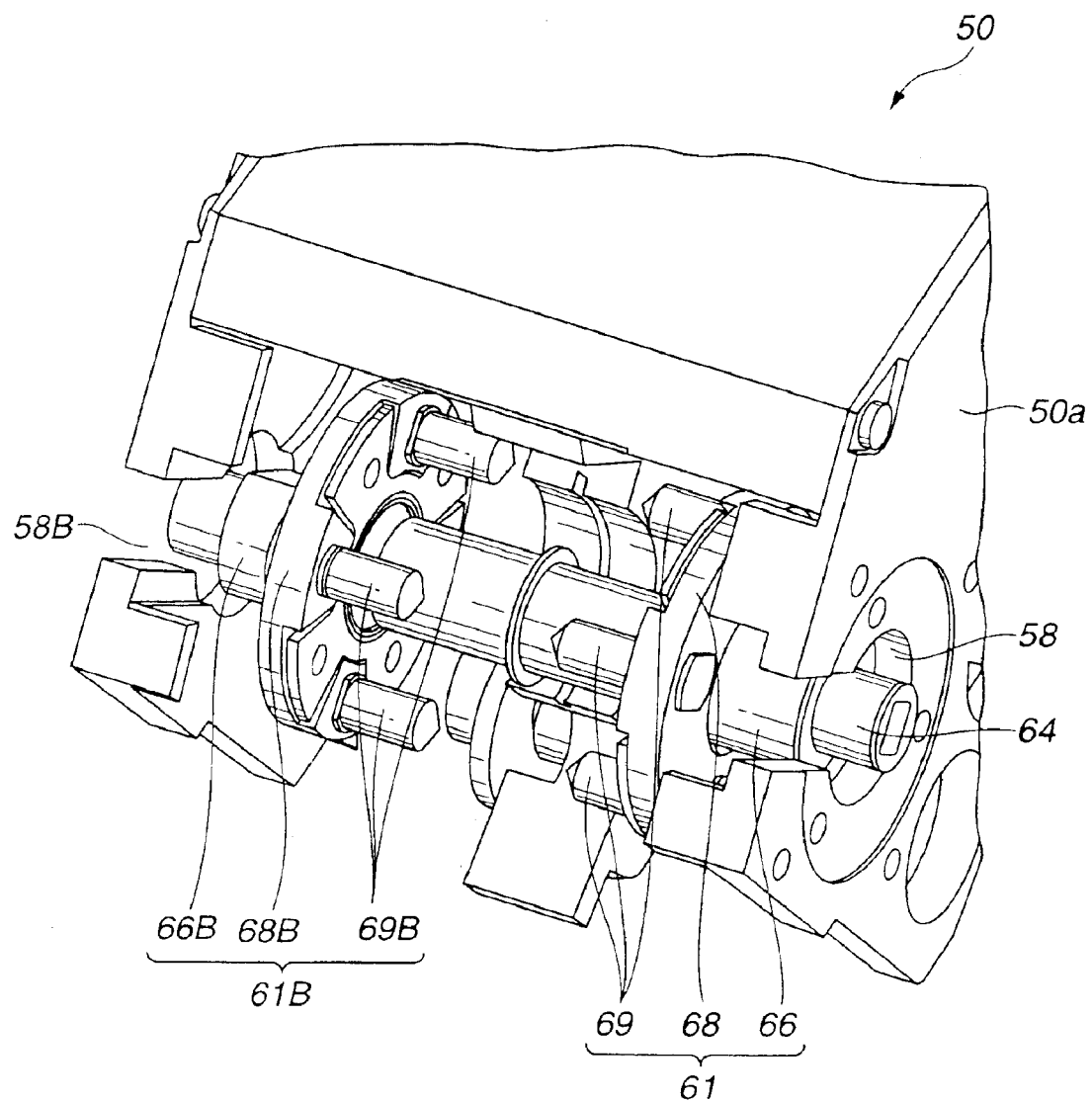
FIG. 10 is a perspective diagram showing a thrust mechanism in FIG. 9.
Figure 11:
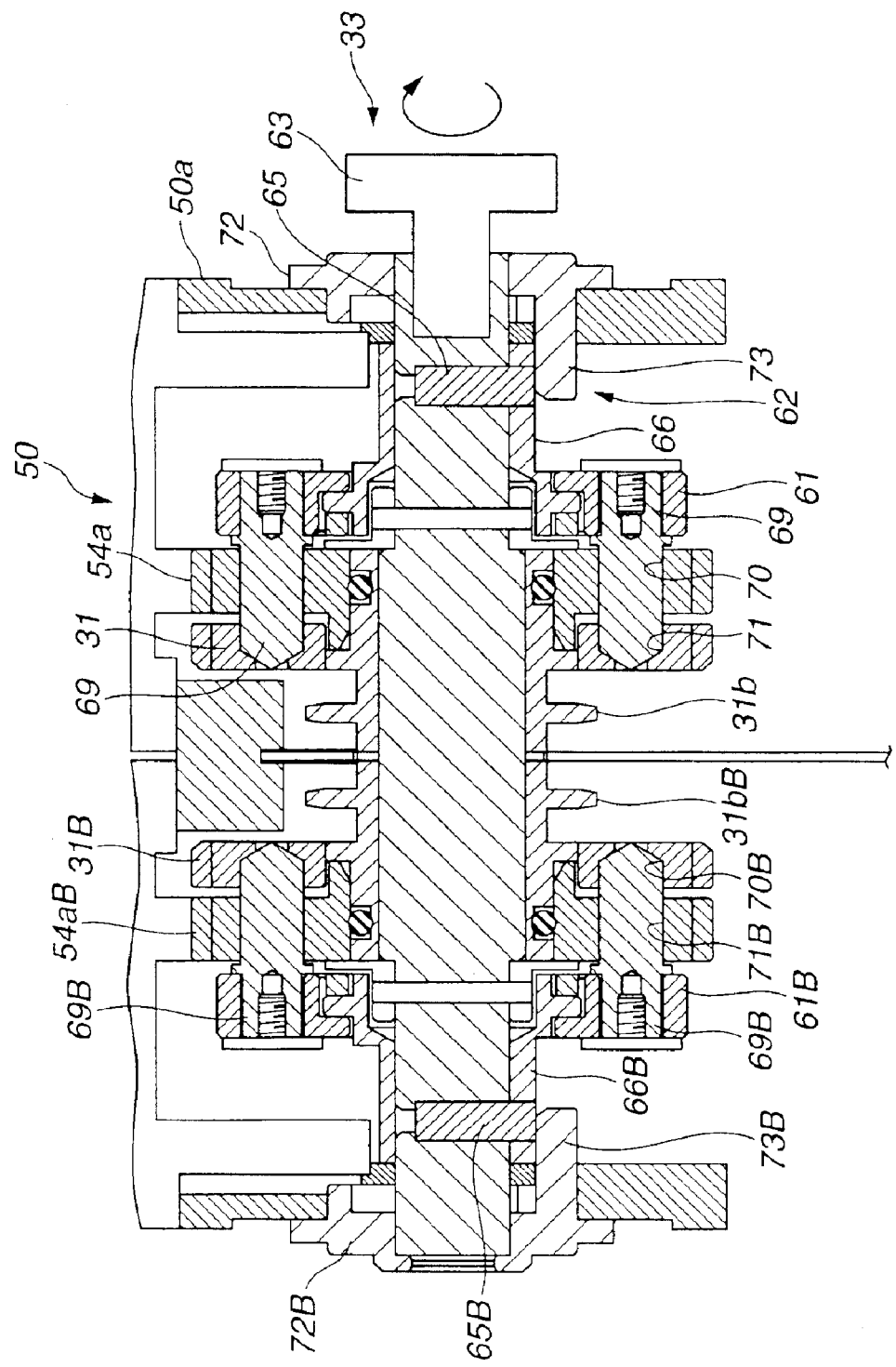
FIG. 11 is a section diagram showing the clutch mechanism allowing the conduction of driving force.

As shown in FIGS. 9 to 11, the final level gear 54a of the gear train 54 and the sprocket 31 are provided coaxially.

The clutch mechanism 33 includes a transmitting member 61, a thrust mechanism 62, and a clutch operation knob 63 (see FIG. 11). The transmitting member 61 connects and disconnects the final gear 54a of the gear train 54 and the sprocket 31, which are provided coaxially. The thrust mechanism 62 moves the transmitting member 61 back and forth in the axial direction of the sprocket 31. The clutch operation knob 63 is connected to the thrust mechanism 62 and functions as a clutch operation member for instructing the connection and disconnection between the final level gear 54a of the gear train 54 and the sprocket 31.

The sprockets 31 and 31B have projections 31b and 31bB for latching the chains 27 on the facing sides, respectively. The chains latching on the projections 31b and 31bB are pulled and are relaxed in accordance with the rotations of the sprockets 31 and 31B so that the bending operation wires 26 can be pulled and be relaxed.

The thrust mechanism 62 is mounted at the opening portion 58 of the gearbox 50 such that a shaft 64 can rotate. The clutch operation knob 63 is connected to the right side end of the shaft 64. The shaft 64 can be rotated in response to manipulations on the clutch operation knob 63.

The shaft 64 has, at the both ends, a cam pin 65 (see FIG. 11) movably fitted to a cam slot, which will be described later, on the transmitting member 61. The sprocket 31, the final level gear 54a of the gear train 54 and the transmitting member 61 are mounted to the shaft 64 from the center toward the both ends.

Figure 12A:
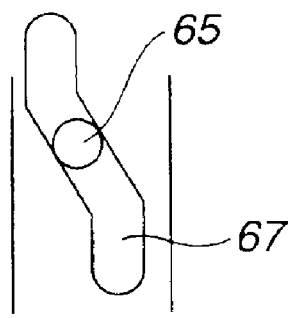
FIG. 12A is an explanatory diagram showing a cam slot on a supporting tube of a first transmitting member.
Figure 12B:
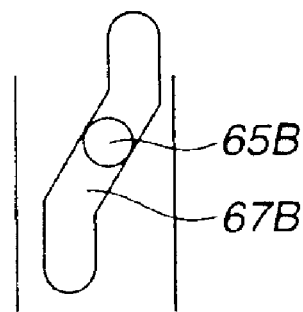
FIG. 12B is an explanatory diagram showing a cam slot on a supporting tube of a second transmitting member.

The transmitting member 61 is held against the shaft 64 by the supporting tube 66 and is a cam (cam structure) having a cam slot 67 in which the cam pin 65 of the shaft 64 is movably fitted to the supporting tube 66. The first cam slot 67 shown in FIG. 12A and the second cam slot 67B shown in FIG. 12B are arranged symmetrically. The thrust mechanism 62 includes a guide member for preventing the rotations of the cam (cam structure) as described later, which establishes a came mechanism.

The shaft 64 is rotated by the manipulation of the clutch operation knob 63 so that the transmitting member 61 can be guided by the cam pin 65 of the shaft 64 movably fitted to the cam slot 67 and can move back and forth in the longitudinal axis direction of the shaft 64.

In the transmitting member 61, a ring portion 68 can rotate about the supporting tube 66. The ring portion 68 has multiple driving force transmitting pins 69 in a circle form on the surface facing toward the final level gear 54a of the gear train 54. The driving force transmitting pins 69 connects and disconnects the final level gear 54a of the gear train 54 and the sprocket 31. Alternatively, one thick driving force transmitting pin 69 may be provided.

The final level gear 54a of the gear train 54 has through portions 70 in a circle form. The driving force transmitting pins 69 of the transmitting member 61 are fitted into the through portions 70. The number of through ports 70 is equal to the number of driving force transmitting pins 69. In the transmitting member 61, the driving force transmitting pins 69 are fitted into the through portions 70 of the final level gear 54a of the gear train 54, and the head protrudes. Thus, when the motor 32 drives, the ring portion 68 in the transmitting member 61 rotates together with the final level gear 54a of the gear train 54.

Figure 13:
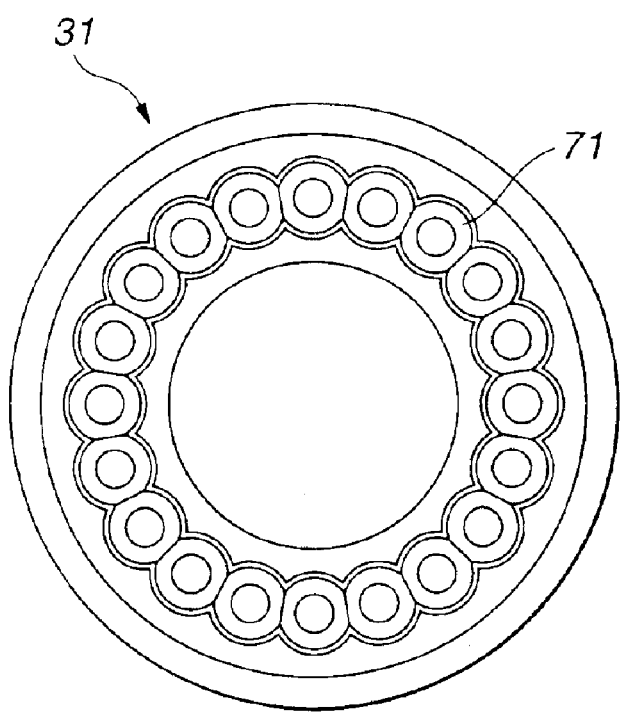
FIG. 13 is an explanatory diagram showing a facing side of a sprocket toward a final level gear of a gear train.

The sprocket 31 has hole portions 71 in a circle form on the side facing toward the final level gear 54a of the gear train 54 as shown in FIG. 13. The heads of the driving force transmitting pins 69 of the transmitting member 61 through the final level gear 54a of the gear train 54 are fitted to the hole portions 71.

The transmitting member 61 moves back and forth in the longitudinal axis direction of the shaft 64. Thus, the heads of the driving force transmitting pins 69 of the transmitting member 61 through the final level gear 54a of the gear train 54 are fitted to the hole portions 71 of the sprocket 31 for connecting and disconnecting the final level gear 54a of the gear train 54 and the sprocket 31.

Also in the second transmitting member 61B, the shaft 64 rotates in response to the manipulation on the clutch operation knob 63. Thus, the same operation is performed simultaneously with the operation of the first transmitting member 61 to connect and disconnect the final level gear 54aB of the second gear train, not shown, and the sprocket 31B.

At the end of the shaft 64, in order to prevent the rotation of the supporting tube 66 with the rotation of the ring portion 68 of the transmitting member 61, a positioning flange 72 is mounted to the gearbox 50. The positioning flange 72 has an extending portion 73 in a D-cut form and also functions as a guide member for guiding the supporting tube 66 of the transmitting member 61 in order to prevent the thrust mechanism 62 from the interference with the gear train 54.

In other words, the thrust mechanism 62 includes the positioning flange 72 also functioning as a guide member for preventing the rotation of the cam (cam structure), which establishes a cam mechanism.

Figure 14:
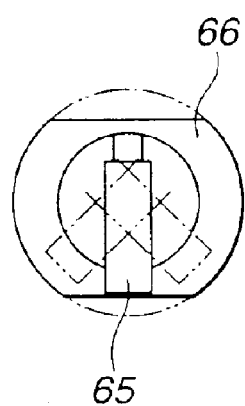
FIG. 14 is an explanatory side elevation diagram showing a supporting tube of a transmitting member.

On the other hand, as shown in FIG. 14, the supporting tube 66 of the transmitting member 61 is provided in a D-cut form to the extending portion 73 of the positioning flange 72. Thus, the thrust mechanism 62 is prevented from interfering with the gear train 54 and can be reduced in size without other devices.

Figure 15:
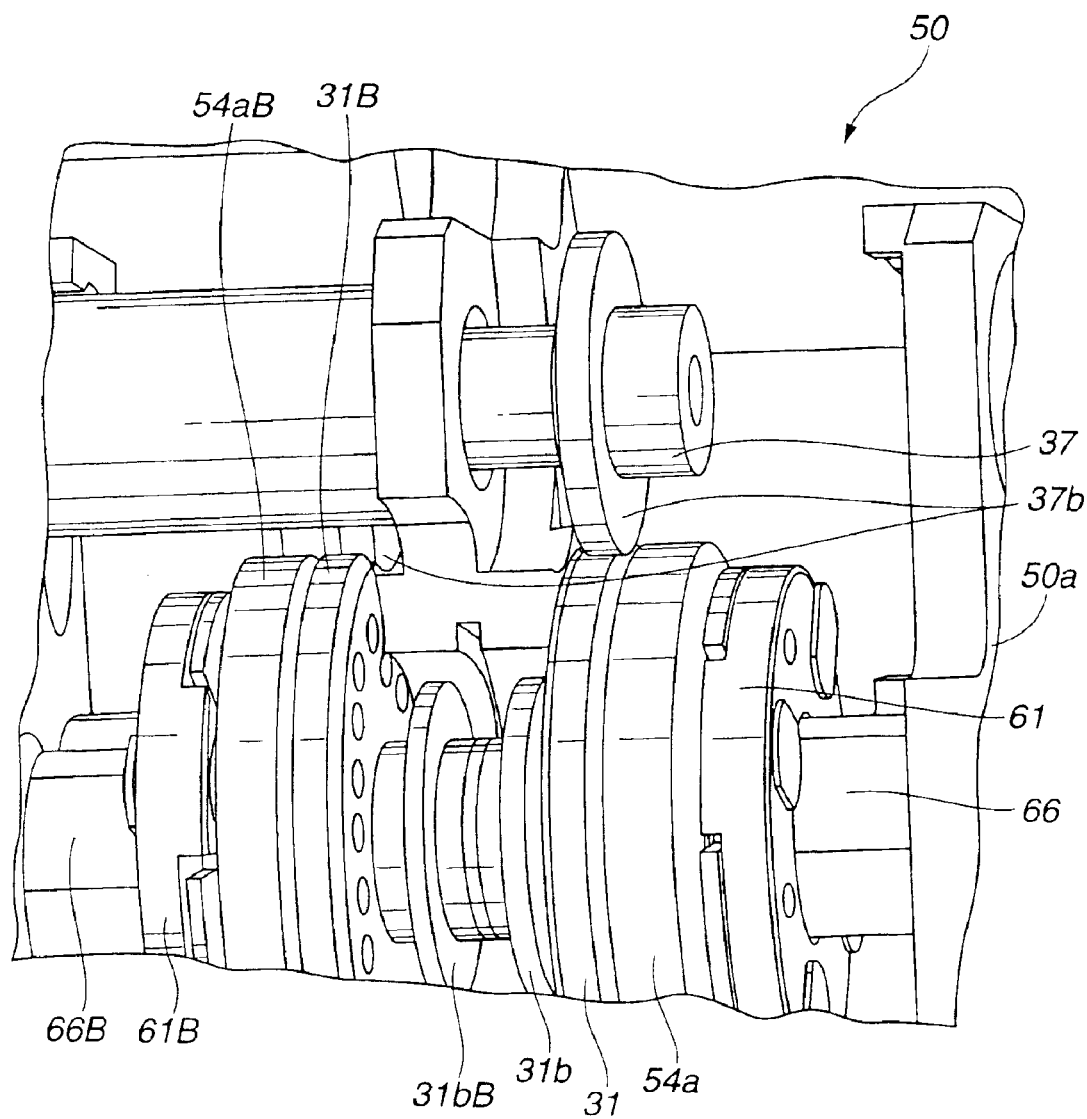
FIG. 15 is a perspective diagram showing a connection between a potentiometer and the sprocket.

The gear of the potentiometer 37 engages with the sprocket 31, as shown in FIG. 15. Thus, the rotational angle of the sprocket 31 and the rotational angle of the potentiometer 37 always have one-to-one correspondence independently from the transmission state of the clutch mechanism 33.

As described with reference to FIG. 1, the electrically-bent endoscope apparatus 1 having the above-described construction can be used for endoscope examinations, for example, by connecting the light source device 3, the video processor 4 and the bending control device 5 to the electrically-bent endoscope 2. In the electrically-bent endoscope 2 before use, the bend driving portion 30 is at the initial state, and the bending portion 12 can be bent. In other words, in the electrically-bent endoscope 2, the transmitting members 61 and 61B of the clutch mechanism 33 are located near the center in the longitudinal axis direction of the shaft 64.

More specifically, in the clutch mechanism 33, the driving force transmitting pins 69 fit into the hole portions 71 of the sprocket 31 to connect the final level gear 54a of the gear train 54 and the sprocket 31. Furthermore, the driving force pins 69B fit into the hole portions 71B of the sprocket 31B to connect the final level gear 54aB of the second gear train and the sprocket 31B.

Under this condition, an operator manipulates the bending operation input portion 20 such as a joystick to bend the bending portion 12 of the electrically-bent endoscope 2 and inserts the inserting portion head portion 11 to the target part in the body cavity.

Here, the control unit 35 of the bending control device 5 turns on the motor amplifier 34 of the vertical and horizontal motors 32 and 32B and reads an instructing value (bending operation signal) instructed by the bend operation inputting portion 20.

The control unit 35 computes the motor rotational angle from the read instructing value (bending operation signal) of the bending operation input portion 20, outputs the computed value to the motor amplifier 34 and instructs the motor rotational angle. Then, the motor amplifier 34 drives the motors 32 and 32B so as to obtain the instructed motor rotational angle.

The driving force of the motor 32 decelerates, is amplified and is transmitted to the sprocket 31 through the clutch mechanism 33. Thus, the sprocket 31 rotates. Then, the chains 27 hung on the sprocket 31 are pulled and relaxed in accordance with the rotation of the sprocket 31 to pull and relax the bending operation wires 26. On the other hand, the same operations are performed on the driving force of the second motor 32B, and the bending portion 12 of the electrically-bent endoscope 2 can perform a predetermined bending operation.

Here, for example, in the middle of an endoscope examination, the bending portion 12 of the electrically-bent endoscope 2 may need to have the angle-free state. The operator can operate the clutch operation knob 63 of the electrically-bent endoscope 2 to operate the clutch mechanism 33. Thus, the driving force of the motors 32 and 32B can be disconnected.

Here, the shaft 64 of the electrically-bent endoscope 2 rotates in response to the manipulation of the clutch operation knob 63. Then, in the electrically-bent endoscope 2, the transmitting member 61 is guided by the cam pin 65 of the shaft 64 movably fitted to the cam slot 67B and is moved to the end in the longitudinal axis direction of the shaft 64. At the same time, the transmitting member 61B is guided by the cam pin 65B of the shaft 64 freely fitted to the cam slot 67B and is moved to the end in the longitudinal axis direction of the shaft 64.

Here, in the transmitting member 61, the supporting tube 66 is guided by the extending portion 73 of the positioning flange 72 and is positioned so as to prevent the thrust mechanism 62 from interfering with the gear train 54. Furthermore, in the transmitting member 61B, the supporting tube 66B is guided by the extending portion 73B of the positioning flange 72B and is positioned so as to prevent the thrust mechanism 62 from interfering with the second gear train.

Then, in the electrically-bent endoscope 2, the head of the driving force transmitting pins 69 of the transmitting member 61 come out from the hole portions 71 of the sprocket 31 to disconnect the final level gear 54a of the gear train 54 and the sprocket 31. Furthermore, the head of the driving force transmitting pins 69B of the transmitting member 61B come out from the hole portions 71B of the sprocket 31B to disconnect the final level gear 54aB of the second gear train and the sprocket 31B.

Therefore, the electrically-bent endoscope 2 enters into a driving-force non-transmission state in which driving forces of the motors 32 and 32B are not transmitted to the sprockets 31 and 31B. Then, the bending portion 12 has the angle-free state. Here, the electrically-bent endoscope 2 rotates such that the sprockets 31 and 31B can rotate in accordance with the load on the bending portion 12.

Then, an operator performs a desired work under this condition, and, after the work, the operator manipulates the clutch operation knob 63 of the electrically-bent endoscope 2 again to return the bending portion 12 to the bendable state. The operator manipulates the clutch operation knob 63 of the electrically-bent endoscope 2 to operate the clutch mechanism 33 so that the driving forces of the motors 32 and 32B can be connected.

Here, the electrically-bent endoscope 2 performs the opposite operation of the above-described operation in response to the manipulation on the clutch manipulation knob 63. Thus, the driving force transmitting pins 69 fit into the hole portions 71 of the sprocket 31, and the final level gear 54a of the gear train 54 and the sprocket 31 can be connected. The driving force transmitting pins 69B fit into the hole portions 71B of the sprocket 31B. As a result, the final level gear 54aB of the second gear train and the sprocket 31B can be connected.

Therefore, the electrically-bent endoscope 2 enters into a driving force transmission state in which the driving forces of the motors 32 and 32B are transmitted to the sprockets 31 and 31B, and the bending portion 12 becomes bendable.

Then, the operator manipulates the bending operation input portion 20 such as a joystick again to bend the bending portion 12 of the electrically-bent endoscope 2.

Here, the control unit 35 of the bending control device 5 detects the rotational angles of the potentiometers 37 and 37B when the clutch mechanism 33 shifts from the driving force non-transmission state to the driving force transmission state. Then, the difference between the information and the amount of the operation of the bend operation input portion 20 are compared in the comparison unit 39, and the control unit 35 realizes the fact.

Here, as described above, the rotational angles of the sprockets 31 and 31B and the rotational angles of the potentiometers 37 and 37B are independent from the transmission state of the clutch mechanism 33, the connection has always one-to-one correspondence.

When the clutch mechanism 33 is in the driving force transmission state, the amount of the operation of the bending operation input portion 20 and the amount of the operation (bending angle) of the bending portion 12 always have one-to-one correspondence.

However, when the clutch mechanism 33 is in the driving force non-transmission state, the amount of the operation of the bending operation input portion 20 and the amount of the operation (bending angle) of the bending portion 12 no longer has a correspondence.

Therefore, when an absolute position input device, for example, such as joystick is used, the control unit 35 notifies the operator of the difference between the information from the potentiometers 37 and 37B and the amount of the operation of the bending operation input portion 20 by driving the warning unit 40 and performing a calibration operation, for example.

On the other hand, when the bending operation input portion 20 is, for example, a speed input device such as a pointing device, the control unit 35 realizes the application. Then, when the bending operation input portion 20 instructs to bend the bending portion 12 to the angle limit and when the bending portion 12 reaches the bendable limit, the control unit 35 outputs a stop signal to the motor amplifier 34. Then, the driving signals to the motors 32 and 32B are stopped. The control unit 35 stores the angle limit of the bending portion 12 in advance.

As a result, the electrically-bent endoscope apparatus 1 according to this embodiment can have the electrically-bent endoscope 2 including the clutch mechanism 33, which has higher stiffness resistance and can be reduced in size.

The electrically-bent endoscope 2 according to this embodiment applies the invention to the electronic endoscope in which the imaging device 24 for imaging a captured object image is contained in the inserting portion head portion 11. However, the present invention is not limited thereto but may be apparently applied to an optical endoscope which has an image transmitting portion for transmitting a captured object image and by which an object image transmitted by the image transmitting portion can be observed through an ocular portion at the operating portion rear end.

The electrically-bent endoscope 2 according to this embodiment is removably connected to the bending control device 5, and the bending control device 5 controls the driving of the bend driving portion 30. However, the present invention is not limited thereto but may contain the bending control device 5.

Apparently, according to the invention, various kinds of different embodiments are possible without departing from the spirit and scope of the invention. The present invention is not limited by the specific embodiments but is only limited by appended claims.

What is claimed is:

1. An electrically-bent endoscope, comprising:
   a motor for generating a driving force;
   a gear train for transmitting the driving force generated by the motor, the gear train having a plurality of gears;
   a converting member for converting the driving force of the motor to a back and forth movement of a bending operation member for bending a bending portion provided at an inserting portion, the converting member and a final level of the gear train being mounted about a common axis;
   a transmitting member for connecting and disconnecting the gear train and the converting member, the driving force being transmitted from the final level of the gear train to the converting member when the transmitting member is connected to the gear train and the converting member;
   a thrust mechanism for moving the transmitting member in an axial direction of the axis; and
   an operating member, connected to the thrust mechanism, for inputting instructions for connecting and disconnecting between the gear train and the converting member.

2. An electrically-bent endoscope according to claim 1, wherein the motor, the gear train, the converting member, the transmitting member and the thrust mechanism are provided in a gearbox.

3. An electrically-bent endoscope according to claim 2, wherein the gearbox is coated with a heat transmitting agent on the side facing toward the motor and also functions as a heat sink.

4. An electrically-bent endoscope according to claim 1, wherein a pinion engaging with the gear train is press-fitted into a motor axis of the motor.

5. An electrically-bent endoscope according to claim 1, further comprising a first detector for detecting a rotating position of the converting member.

6. An electrically-bent endoscope according to claim 5, further comprising:
   a second detector for detecting a rotating position of the motor axis, a comparison unit for comparing information from the first detector and information from the second detector in order to detect the bending limit of the bending portion, and a warning unit for warning an operator based on the comparison result by the comparison unit.

7. An electrically-bent endoscope according claim 6, further comprising a control portion for terminating the motor when the comparison unit detects that the bending portion reaches the bending limit.

8. An electrically-bent endoscope according to claim 6, wherein the motor and the second detector are detachable from the gearbox.

9. An electrically-bent endoscope according to claim 8, wherein the transmitting member and the thrust mechanism constitute a clutch mechanism, and the clutch mechanism is provided in the gearbox such as to be detachable from the gear train.

10. An electrically-bent endoscope according to claim 9, wherein the thrust mechanism is a cam mechanism including a cam pin provided at a shaft rotating in response to a manipulation on the clutch operation knob, a cam having, in the transmitting member, a cam slot to which the cam pin freely fits, and a slide guide for preventing the rotation of the cam,
   wherein the transmitting member moves back and forth in the longitudinal axis direction of the shaft in response to an operation of the cam mechanism and has one or more driving force transmitting pins for removably connecting and disconnecting the final level of the gear train and the sprocket, wherein the final level of the gear train has one or more through portions through which the driving force transmitting pins of the transmitting member are inserted, wherein the sprocket has one or more hole portions to which the driving force transmitting pins through the final level of the gear train fit.

11. An electrically-bent endoscope according to claim 5, wherein a gear engaging with the sprocket contains aluminum in the first detector.

12. An electrically-bent endoscope according to claim 11, wherein the gearbox covers the gear train.

13. An electrically-bent endoscope according to claim 5, wherein the transmitting member and the thrust mechanism constitute a clutch mechanism, and the clutch mechanism is provided in the gear box such as to be detachable from the gear train.

14. An electrically-bent endoscope according to claim 13, wherein the gear box has an opening to remove the transmitting member and the thrust mechanism from the gear box.

15. An electrically-bent endoscope according to claim 1, wherein the thrust mechanism has a cam mechanism including a cam pin provided at a shaft to be rotated in response to a manipulation of the operating member, a cam, provided in the transmitting member, having a cam slot for fitting the cam pin, and a guide member for preventing the rotation of the cam.

16. An electrically-bent endoscope according to claim 15, wherein the transmitting member has driving force transmitting pins for moving in the longitudinal axis direction of the shaft in response to the operation of the cam mechanism and being inserted to holes in the final level of the gear train and the converting member such that driving force transmitted from the final level of the gear train to the converting member can be connected and be disconnected.

17. An electrically-bent endoscope according to claim 16, wherein the guide member also functions as a positioning flange for preventing the rotation of the cam in the transmitting member.

18. An electrically-bent endoscope according to claim 17, wherein the transmitting member and the thrust mechanism constitute a clutch mechanism, and the clutch mechanism is provided in the gearbox such as to be detachable from the gear train.

19. An electrically-bent endoscope, comprising:
a motor for generating a driving force for bending a bending portion provided at an insertion portion;
a gear train for transmitting the driving force generated in the motor;
a sprocket for converting the driving force of the motor to a back and forth movement of a bending operation wire, the sprocket and a final level of the gear train being mounted about a common axis for rotation;
a transmitting member for connecting and disconnecting the final level of the gear train and the sprocket, the driving force being transmitted from the final level of the gear train to the sprocket when the transmitting member is connected to the gear train and the sprocket;
a thrust mechanism for moving the transmitting member back and forth in an axial direction of the axis for rotation in order to connect and disconnect the final level of the gear train and the sprocket; and
a clutch operation knob, connected to the thrust mechanism, for inputting instructions for connecting and disconnecting between the gear at the final level of the gear train and the sprocket.

20. An electrically-bent endoscope, comprising:
a motor for generating a driving force;
a driving force transmitting portion for transmitting the driving force generated by the motor, the driving force transmitting portion having an output member mounted to a shaft for outputting the transmitted driving force;
a converting portion for converting the driving force of the motor outputted by an output member to a back and force forth movement of a bending operation member for bending a bending portion provided at an insertion portion;
a transmitting member for connecting and disconnecting the output member and the converting portion;
a thrust portion for moving the transmitting member in an axial direction of the shaft in order to connect and disconnect the output member and the converting portion;
an operating portion, connected to the thrust portion, for inputting instructions for connecting and disconnecting between the driving force transmitting portion and the converting portion.

21. An electrically-bent endoscope, comprising:
a motor;
driving force transmitting means for transmitting a driving force generated by the motor, the driving force transmitting means having an output member mounted to a shaft for outputting the transmitted driving force;
converting means for converting the driving force of the motor to a back and forth movement of a bending operation member for bending a bending portion provided at an insertion portion of the endoscope;
a transmitting member for connecting and disconnecting the driving force transmitting means and the converting means;
means for moving the transmitting member in an axial direction of the shaft in order to connect and disconnect the output member and the converting means; and
operating means, connected to the means for moving the transmitting member, for inputting instructions for connecting and disconnecting between the driving force transmitting means and the converting means.

22. An electrically-bent endoscope, comprising:
a motor for generating a driving force;
a gear train for transmitting the driving force generated by the motor;
a converting member for converting the driving force of the motor to a back and forth movement of a bending operation member for bending a bending portion of an inserting portion of the endoscope a head side of the inserting portion;
a clutch mechanism having a transmitting member for connecting and disconnecting the gear train and the converting member, the clutch mechanism connecting and disconnecting the driving force transmitted from the gear train to the converting member;
a thrust mechanism for moving the transmitting member in an axial direction relative to of the converting member; and
a clutch operating member, connected to the thrust mechanism, for inputting instructions for connecting and disconnecting between the gear train and the converting member, wherein a final level of the gear train and the transmitting member are provided coaxially, and the thrust mechanism has a cam mechanism including a cam pin provided at a shaft to be rotated in response to a manipulation on the clutch overacting member, a cam provided in the transmitting member, the cam having a cam slot for fitting the cam pin, and a guide member for preventing rotation of the cam.

23. An electrically-bent endoscope according to claim 22,
wherein the transmitting member has a driving force transmitting pins for moving in the longitudinal axis direction of the shaft in response to the operation of the cam mechanism and being inserted to holes in the final level of the gear train and the converting member such that driving force transmitted from the final level of the gear train to the converting member can be connected and be disconnected.

24. An electrically-bent endoscope according to claim 23,
wherein the guide member of the clutch mechanism also functions as a positioning flange for preventing the rotation of the cam in the transmitting member.

25. An electrically-bent endoscope according to claim 24,
wherein the clutch mechanism is detachable from a gearbox in which the motor, the gear train, the converting member and the clutch mechanism are provided.

26. An apparatus for bent-driving an endoscope, comprising:
   a gear train for transmitting driving force generated by a motor, the gear train having a plurality of gears;
   a converting member for converting the driving force of the motor to a back and forth movement of a bending operation member for bending a bending portion provided at an insertion portion of the endoscope, the converting member and a final level of the gear train being mounted about a common axis;
   a transmitting member for connecting and disconnecting the gear train and the converting member, the driving force being transmitted from the final level of the gear train to the converting member when the transmitting member is connected to the gear train and the converting member;
   a thrust mechanism for moving the transmitting member in an axial direction of the axis; and
   an operating member connected to the thrust mechanism for inputting instructions for connecting and disconnecting between the gear train and the converting member.

* * * * *